United States Patent [19]

Wood et al.

[11] Patent Number: 4,960,699
[45] Date of Patent: Oct. 2, 1990

[54] ENZYMATIC DEPOLYMERIZATION OF COAL

[75] Inventors: Willis A. Wood, Cardiff; Lillian M. Wondrack, San Diego, both of Calif.

[73] Assignee: Salk Institute Biotechnology/Industrial Associates, Inc., San Diego, Calif.

[21] Appl. No.: 193,332

[22] Filed: May 9, 1988

[51] Int. Cl.$^5$ .................... C12R 1/645; C12P 1/02; C12P 5/00; C12N 9/08

[52] U.S. Cl. ......................... 435/166; 435/41; 435/131; 435/132; 435/171; 435/192; 435/254; 435/911

[58] Field of Search ................. 435/41, 911, 166, 171, 435/192, 254, 131, 132

[56] References Cited

U.S. PATENT DOCUMENTS 4,052,448 10/1977 Schulz et al.
4,137,418 1/1979 Schulz et al.
4,235,728 11/1980 Schulz et al.
4,687,741 8/1987 Farrell et al.

OTHER PUBLICATIONS

Chem. Abs. 110(1989) 138460w Scott et al. Appl. Biochem. Biotech. 1988, 18, 403–12.
Derwent Abst. 88-063976/89 Aust. et al. WO88012-(2-1988).
Derwent Chem. Abs. CA11-100124(12) Maka et al. Appl. Bioch. Biotech. 1989, vol. 20–21, pp. 715–729 (1989).
Leisola, M., et al., "Strategies for Production of High Ligninase Activities by Phanerochaete chrysosporium", J. Biotechnology 3, 97–107 (1985).
Cohen, M. S. et al., "Cell-Free Solubilization of Coal by Polyporus versicolor" Applied Environ. Microbiol. 53, 2840–2843 (1987).
Chowdhury, J. K. et al., "Studies on Aerial Oxidation of Coal with Special Reference to the Distribution of Oxygen and Carbon in Coal and its Oxidation Products", J. Indian Chem. Soc. 19, 289–298 (1942).
Juettner, B. et al., "The Action of Nitric Acid on a Bituminous Coal", J. Am. Chem. Soc. 57, 2322–2326 (1935).
Charmbury, H. B. et al., "The Chemistry of Nitrogen in Humic Acids from Nitric Acid Treated Coal", J. Am. Chem. Soc. 67, 625–628 (1945).
Scott, C. D. et al., "Microbial Solubilization of Coal", Biotech. Prog. 2, 131–139 (1986).
"Process Yields Diesel-Like Fuel from Coal, Peat, Biomass", Chemical and Engineering News, pp. 23–24, (Jul. 1, 1985).

Primary Examiner—Herbert J. Lilling
Attorney, Agent, or Firm—Fitch, Even, Tabin & Flannery

[57] ABSTRACT

A method is provided for converting coal to low molecular weight organic compounds comprising combining an aqueous solution of an aqueous-soluble polymeric coal substrate with a lignin peroxidase, oxygen and hydrogen peroxide. The invention is exemplified using the lignin peroxidase from Phanerochaete chrysosporium. Also provided are aqueous-soluble polymeric coal substrates suitable for lignin peroxidase-catalyzed depolymerization and methods of preparing such substrates. Finally, a method is provided for isolating the lignin peroxidase from mycelia-free, unconcentrated media of cultures of *P. chrysosporium* producing the enzyme.

4 Claims, No Drawings

ENZYMATIC DEPOLYMERIZATION OF COAL

FIELD OF THE INVENTION

This invention relates generally to a method for depolymerizing coal, and, more specifically to the use of enzymes to catalyze the depolymerization of coal.

BACKGROUND OF THE INVENTION

For more than 100 years, chemicals obtained as by-products in the primary processing of coal to coke have been the main source of aromatic compounds used as intermediates in the synthesis of dyes, drugs, antiseptics, solvents and other products. Although some aromatic hydrocarbons, such as toluene and xylene, are now obtained largely from petroleum refineries, the main source of many others is still the coke oven.

Unfortunately, in addition to producing important products by depolymerization of coal, the refineries and by-product coke ovens, by their mode of operation, also unavoidably and largely uncontrollably discharge, to the environment, enormous quantities of heat and materials hazardous to the environment and to human health. Operation of by-product coke ovens requires high temperatures, which favor the formation of high molecular weight "ring" compounds, of limited practical value, such as anthracenes, fluoranthracene, pyrene, benzanthracene, dibenzanthracene, benzpyrene, and the like, and inhibit the formation of more useful, low molecular weight compounds such as phenols, benzoic acid, phthalic acid, other carboxylic acids, and the benzylic alcohols containing simple aromatic ring systems. As a result, it would be advantageous if coal could be subjected to low temperature depolymerization processes to yield compounds such as the aforementioned, more useful ones.

Enzymes are known that catalyze the depolymerization of various biopolymers. Further, enzymatically catalyzed reactions occur typically at low temperatures, between about 20° and about 70° C, and, hence, do not have the potential of stressing the environment in ways that are associated with traditional coal processing. Heretofore, however, no enzyme has been known to catalyze depolymerization of coal.

Two reasons for the absence of recognition in the art of coal depolymerization-catalyzing enzymes are that enzymes function best in aqueous environments and that enzymes require soluble substrates in order to catalyze reactions at high rates. Thus, heretofore, the insoluble nature of coal has presented the potential enzyme depolymerization catalyst with an intractable substrate such that, even with increases in surface area furnished by grinding coal into small particles, reaction rates indicative of enzymatic catalysts could not have been observed, even if enzymatically catalyzed reactions were occurring. The discovery of the present invention, of high molecular weight coal substrates that are soluble in aqueous solution under conditions suitable for enzymatic activity, has made possible the discovery of the invention, that certain enzymes catalyze coal depolymerization.

SUMMARY OF THE INVENTION

The invention entails a novel method for depolymerizing coal. According to the method, an aqueous solution of polymers, which are extracted from coal, serves as substrate for a lining-degrading enzyme, generally referred to as a ligninase or lignin peroxidase. When combined with hydrogen peroxide and oxygen in an aqueous reaction mixture, the enzyme catalyzes the depolymerization of the soluble, polymeric coal extract.

Prior to the present invention, it was not realized that the degradation of coal could be enzymatically catalyzed.

According to the invention, the coal is first fractionated to yield a novel, water-soluble, polymeric coal subfraction, which subfraction is soluble at low pH and is a substrate suitable for the ligninase. The invention also entails these novel, water-soluble polymeric subfractions of coal.

The polymeric subfraction substrate is reacted with oxygen in a depolymerization reaction catalyzed by a ligninase (in the presence of $H_2O_2$) to effect the depolymerization of the coal.

An example of a lignin-degrading enzyme, which can be employed in coal depolymerization in accordance with the invention, is the lignin peroxidase of the basidiomycete Phanerochaete chrysosporium, which is known to catalyze a variety of degradation reactions on lignin, and substructures related to lignin, in the presence of oxygen and nonstoichiometric amounts of $H_2O_2$. These include, among others, $C_{alpha}$-$C_{beta}$ cleavage, and beta-0-4 ether bond cleavage of diarylpropane diols and triols, oxidation of benzylic-carbinols to oxo compounds, formation of cyclic ketals, and aromatic ring cleavage reactions. Another important reaction is the oxidation of veratryl alcohol to veratraldehyde, which provides the basis for a simple spectrophotometric assay for the enzyme. Lignin and its substructures are stereoirregular polymers, in that there is no systematic arrangement of the chiral carbon atoms therein. Thus, lignin peroxidase is unusual among enzymes in being able to accept diverse structures as substrates and catalyze a seemingly diverse set of reactions.

Microorganisms, and especially fungi of numerous species in the class Basidiomycete, as well as other species, are known which decompose wood, including the lignin component thereof. From these fungi, including P. chrysosporium, enzymes ("ligninases") have been isolated which decompose lignin in wood, and model substrates of lignin, in the presence of $H_2O_2$ and $O_2$. See, e.g., Tien and Kirk, Proc. Natl. Acad. Sci. (USA) 81, 2280–2284 (1984); Farre)1 et al., U.S. Pat. No. 4,687,741; Srinivasan et al , U.S. Pat. No. 4,713,336: Buswell and Odier, French Patent Application Publication No. 2,574,427.

The present invention rests in part on the unexpected discovery that these lignin-degrading enzymes can also catalyze the depolymerization of a coal substrate (i.e., polymeric coal subfraction, which is soluble in an aqueous solution at low pH).

Depolymerization in accordance with the invention is carried out at temperatures, generally between about 20°–50° C., preferably around 37° C. Since these temperatures are significantly lower than those employed in traditional methods for converting coal to organic compounds, the method of the invention is especially useful for converting coal to certain low molecular weight compounds, the formation of which is not favored or is entirely impossible, when coal is subjected to degradation at high temperatures, as in coke ovens.

Lignin peroxidase has traditionally been isolated from mycelia-free culture media of cultures of Phanerochaete in a multi-step process, extending over 1½ to 2 days and comprising concentration of culture medium by ultrafiltration, followed by dialysis of the supernatant from the ultrafiltration, and then DEAE-cellulose chromatography of the concentrated medium. In addition to the long time required for the entire process, the ultrafiltration step leads to an irretrievable loss of at least 40% of the lignin peroxidase in the enzyme-containing culture medium. Following the concentration by ultrafiltration and dialysis, the solution with the remaining enzyme is chromatographed on DEAE-cellulose and specifically eluted therefrom. Typically not more than about 50-60% of the initial amount of lignin peroxidase in a sample of mycelia-free culture medium is recoverable by this traditional, prior art process for isolation of the enzyme.

The present invention also encompasses a novel method, for purification of lignin peroxidase from mycelia-free culture media, which provides a surprisingly high recovery of about 90 % of lignin peroxidase from the media in a process that can be completed advantageously quickly, in 2 to 3 hours. This method of the invention comprises simply chromatographic purification of lignin peroxidase from mycelia-free culture media, of cultures of fungi producing the enzyme, without time-consuming and yield-reducing concentration of the media, and separation of the lignin peroxidase in the media from various other components therein, by ultrafiltration and dialysis prior to the chromatography. The method of the invention employs a substantially incompressible, high flow-rate DEAE-derivatized affinity chromatography matrix to efficiently bind the lignin peroxidase from the media passed through the matrix.

DETAILED DESCRIPTION OF THE INVENTION

In one of its aspects, the method of the invention is based on the surprising discovery that ligninases (e.g., lignin peroxidases of white-rot basidiomycetes), which are known to catalyze the degradation of lignin, are also capable of catalyzing the depolymerization of an aqueous-soluble, polymeric coal substrate into lower molecular weight organic components.

A method of the invention therefore rests as well on the discovery that polymeric coal extracts can be prepared which are suitable as substrates for depolymerization catalyzed at observable rates by ligninases, in that the extracts are soluble in aqueous solution at suitable pH values and temperatures.

Thus, in one of its aspects, the invention is a method of catalyzing the enzymatic depolymerization of polymeric coal substituents comprising combining a ligninase and an aqueous-soluble polymeric coal substrate in an aqueous solution suitable for carrying out enzymatic reactions with the ligninase.

In another of its aspects, the invention is an aqueous-soluble polymeric coal substrate for depolymerization by ligninase, which substrate is made by a method comprising (a) oxidizing coal powder with nitric acid at a temperature between about 15° C and about 70° C; (b) suspending the nitric acid-oxidized coal powder of step (a) in an aqueous solution comprising an alkali metal hydroxide at a concentration to provide a pH of at least 10; (o) separating solids from the suspension of step (b); (d) acidifying the supernatant from (c) to a pH between 2.5 and 3.5 with a strong acid; and (e) extracting the precipitate of step (d) with an aqueous solution with an ionic strength of less than 0.15 molal. The composition extracted into solution in step (e) is the aqueous-soluble polymeric coal substrate.

Another aspect of the invention is the just described method of making the aqueous-soluble polymeric coal substrate of the invention.

A further aspect of the invention is a method for recovering lignin peroxidase directly from unconcentrated, lignin peroxidase-containing, mycelia-free culture medium of a culture of a fungus making the enzyme, which method comprises passing said mycelia-free medium over a DEAE-derivatized, insoluble support material, which comprises an essentially incompressible matrix that is permissive of high flow rates of liquids and is not clogged by the medium. One such support material is a DEAE-derivatized Kieselguhr-cross-linked-agarose matrix, with between about 1% (w/w) and about 10% (w/w) agarose After passing such medium over the DEAE-derivatized material (preferably held in a chromatography column), lignin peroxidase is eluted from the material by ion exchange. This method of the invention is an improvement over prior art methods, employing chromatography over DEAE-derivatized, insoluble support materials, for recovering lignin peroxidase from mycelia-free culture media of fungal cultures in which lignin peroxidases are produced. In the method of the invention, after the culture medium is made mycelia-free by any standard method (e.g., passing through glass wool), the medium is diluted between 0-fold (no dilution) and about 10-fold with a buffer and then simply passed over the DEAE-derivatized support. In contrast, in the prior art methods, after the medium is made mycelia-free and before it is applied to a DEAE-derivatized support material, it is concentrated and freed of various components by ultrafiltration and dialysis.

Lignin is a major, polymeric component of wood, but does not occur among the complex polymers of organic compounds which occur in coal.

The method of the invention for depolymerizing coal is applicable to substrates which are polymeric extracts of coal that are soluble in aqueous solutions in which a ligninase is catalytically active. As indicated above, such coal polymeric extracts and the method of making them are encompassed by the invention. As described in the examples, such fractions have been obtained from lignite coal and subbituminous coal from diverse geographical and geological sites.

Preparation of aqueous-soluble, polymeric coal substrates suitable for enzymatically catalyzed depolymerization will be discussed before discussing preparation of the coal-degrading enzyme and the depolymerization process.

Coal is basically a vitreous, solid chemically heterogeneous polymer formed from peat. Since reactions catalyzed by enzymes proceed at high rates with substrates that are dissolved in aqueous solution, and only slowly (usually unobservably over time intervals of practical significance) on substrates which are part of or embedded in surfaces of insoluble particles, coal samples must be processed to yield aqueous-soluble polymer subfractions that are capable of being efficiently depolymerized in a reaction catalyzed by a coal-degrading enzyme. Such processing usually begins with a processed coal composition that is known to yield material that is soluble in aqueous solution but under conditions (e.g., high pH) at which an enzyme is inactive. Such processed coal composition can be made by: (1) pulverizing or otherwise grinding a coal sample to form a powder and, (2) oxidizing the resulting coal powder, such as by mild oxidation as with nitric acid. As known in the art, treatment of such an oxidized powder with aqueous sodium hydroxide, or other alkali metal hydroxide, extracts material from the powder into solution. Known methods for oxidizing coal with nitric acid are discussed in Example One. Other treatments are known in the art, such as reduction with potassium crown ethers, which solubilize fractions of coal without oxidation.

It is known that treating a carbonaceous material, such as coal, with limited amounts of nitric acid at temperatures below about 100° C. can cause oxidation of methylene groups to carboxyl groups without appreciable ring nitration. Such oxidations are beneficial when processing coal to obtain low molecular weight organic compounds such as oxygen-containing derivatives of the following aromatic compounds: 2,4-cyclopentadiene; methyl pyridines; biphenyls; indenes and thioindenes; anthracenes; phenanthrenes; benzofurans; carbazoles; dibenzothiophenes; fluorenes; and thio- and amino-chrysenes. Carboxylic acids, such as benzoic, phthalic and mellitic, can also be obtained through such oxidations.

We have discovered surprisingly that a coal polymer subfraction, which is part of the fraction rendered soluble by treatment of coal powder with aqueous base after carboxylation with nitric acid at a temperature between about 15° C. and about 70° C, is soluble at low pH values in a low ionic strength aqueous solution.

Prior to being enzymatically depolymerized according to the invention, the processed, high pH-aqueous-soluble coal extract needs to be fractionated or extracted further to produce a polymeric extract that is soluble in aqueous medium under conditions of pH, ionic strength, temperature and the like suitable for activity of the enzyme to be used. Thus, the parameters, such as pH and ionic strength, within which the coal-degrading enzyme is active will dictate, in part, the physical and chemical characteristics that a suitable coal substrate will have. For example, the requirement of a pH of approximately 3.0–3.5 and ionic strength below about 0.1 molal for optimal activity of the P. chrysosporium lignin peroxidase prepared as described in Examples Six and Seven at temperature and pressures of interest (20° C. to 50° C; ambient atmospheric pressure) limits coal substrates ideal for that enzyme to those that are readily soluble in an aqueous solution at 20° C.–50° C. and atmospheric pressure at a pH of about 3.0–3.5 and an ionic strength of about 0.05 to 0.15 molal.

The method of the invention is illustrated using (1) lignin peroxidase derived from *Phanerochaete chysosporium*, and (2) an aqueous-soluble polymeric coal extract substrate according to the invention, that is derived by fractionating pulverized, nitric acid-treated samples of North Dakota lignite or German subbituminous coal to obtain a polymeric material soluble at room temperature and atmospheric pressure in an aqueous solution having a pH of about 2.5–5.0 and an ionic strength between about 0.05 and about 0.15 molal.

Examples One, Two and Four describe methods for preparing aqueous polymeric coal extracts suitable as substrates for depolymerization at significant, readily observable rates by ligninases. It is apparent from those examples that closely similar methods yield suitable, aqueous-soluble polymeric coal substrates, that are susceptible to enzymatic depolymerization by ligninase, from coal samples with differing physical properties, such as those that are known to exist between North Dakota lignite and German subbituminous coal.

Examples Two and Four are intended to make apparent to those of ordinary skill in the art that the solubilities of substantial amounts of polymeric coal substituents, present among the components of oxidized coal powder which are solubilized in an aqueous alkaline solution (pH greater than about 10), are responsive at low pH in aqueous solution to changes in ionic strength. In particular, polymeric coal substituents suitable for depolymerization catalyzed by a ligninase can be obtained by acidifying, to a pH below about 5, with a strong acid such an aqueous alkaline solution and then extracting, with an aqueous solution at low pH and low ionic strength (less than about 0.25 molal), the precipitate that forms upon such acidification of the alkaline solution.

Although desired polymeric substituents of coal are precipitated by simply acidifying said aqueous alkaline solution to a pH below about 5, as just described, yield of such precipitate (and, therefore, polymeric substituents for enzymatically catalyzed depolymerization) is increased by adding salt (preferably of a strong base and a strong acid) to the acidified solution, if necessary in view of the pH of the initial alkaline solution, to bring the concentration of salt in the acidified solution to at least 1 molar. The concentration of added salt can be brought to any level less than saturation, of itself or any salt formed by any of its ions and any of the ions of the base used to increase the pH of the alkaline solution or the acid used in acidifying the alkaline solution. It is preferred that the final concentration of the salt, preferably of a strong base and a strong acid and most preferably of NaCl, be about 1 molar in the acidified solution from which the polymeric coal substituents are precipitated prior to extraction with a low pH, low ionic strength aqueous solution.

By "strong base" is meant a compound which, when dissolved in distilled water, yields nearly an equivalent of hydroxyl ions up to a concentration of at least 0.1 M. Preferred among strong bases for use in accordance with the invention are the alkali metal hydroxides, including NaOH and KOH. Most preferred is NaOH. By "strong acid" is meant a compound which, when dissolved in distilled water, yields nearly an equivalent of hydronium ions up to a concentration of at least 0.1 M. Preferred among strong acids for use in accordance with the invention are the hydrogen halides, including HCl and HBr, and nitric and sulfuric acids. Most preferred is HCl.

As Examples Two and Four demonstrate, the precipitating conditions can be attained by solubilizing the oxidized polymeric coal substituents in, for example, 1 N NaOH (or other alkali metal hydroxide), so that upon acidification with (preferably) a strong acid, the solution will be about 1 molar with respect to the salt of the acid and NaOH. Or, as is the preferred method, the oxidized, pulverized coal may be solubilized in a dilute NaOH (or other alkali metal hydroxide) solution, with the pH of said solution greater than about 10, and preferably between about 10 and about 11. The alkaline solution of coal polymeric substituents can then be acidified to below about pH 5 by addition of (preferably) a strong acid, which will result in some precipitation of said substituents, and then further precipitation can be caused by adding a salt (preferably that of the alkali metal hydroxide with the strong acid) to increase the salt concentration to at least 1 molar, but not greater than the solubility of the salt.

The polymeric substrate for depolymerization catalyzed by a ligninase is then obtained by extracting the precipitate with an aqueous solution of pH between about 2.5 and about 5.0 and ionic strength less than about 0.15 molal; the polymeric material extracted into solution by this step is the polymeric substrate for the enzymes.

The solution containing the extracted material can optionally be dialyzed against low pH, low ionic strength solution prior to introduction of enzyme.

Preferred for use in accordance with the instant invention are coals, such as North Dakota lignite and German subbituminous, which are classified as "lower ranked" coals and characteristically have a higher abundance of methylene groups and oxygen-containing functionalities in their chemical structures than do "higher ranked" coals.

Any enzyme with ligninase activity can be used in the method of the invention. The enzyme can be obtained by culturing organisms which naturally produce such an enzyme. See, e.g., Tien and Kirk, Farrell et al., Srinivasan et al. and Buswell and Odier, supra, and Examples Six and Seven hereinbelow. Alternatively, an organism, such as a yeast of genus Saccharomyces or Pichia, for which suitable transformation systems are available, can be transformed to express a cDNA coding for a ligninase of another species and transformants (or progeny thereof wherein the cDNA is expressed) can be cultured to provide the ligninase. See, e.g., Tien and Tu, Nature 326, 520–523 (1987) and Nature 328, 742 (1987); de Boer et al., Gene 60, 93–102 (1987); Zhang et al., Biochem Biophys Res. Commun. 137, 649–656 (1986). Use of lignin peroxidase derived from cultures of Phanerochaete chrysosporium is preferred.

The enzyme, either in a solution or immobilized on a matrix, as is known in the art, can be combined with the aqueous reaction mixture, which includes the coal subfraction substrate.

Although lignin peroxidase requires hydrogen peroxide ($H_2O_2$) and oxygen ($O_2$) for activity, excess quantities of H202 are known to inactivate the enzyme. For example, the oxidation of veratryl alcohol by lignin peroxidase over a period of 24 hours shows higher activity when $H_2O_2$ is added in small quantities over the course of the reaction than when a single, large aliquot of $H_2O_2$ is added at the initiation of the reaction. Thus, regulating the concentration of $H_2O_2$ to avoid an excess in a reaction mixture will increase the half-life of lignin peroxidase in the mixture.

The concentration of $H_2O_2$ can be maintained at an adequate level, and avoidance of excessive enzyme-inactivating concentrations is facilitated, by generation of the $H_2O_2$ in situ in a reaction catalyzed by an enzyme which functions in the pH range of 3–5, e.g., D-amino acid oxidase. Other $H_2O_2$-producing enzymes may also be used.

Oxygen is also required for lignin peroxidase activity. It can be supplied by introducing solutions of oxygen in emulsions of perfluorocarbons or low viscosity silicone oils into the reaction mixture, or by bubbling or otherwise purging oxygen (preferably 100%) into the reaction mixture.

Lignin peroxidase binds strongly to coal substrate, as evidenced by the ability of coal substrate at low concentrations to inhibit the oxidation of veratryl alcohol by the enzyme. The inhibition is competitive in nature, which indicates that coal substrate occupies the active site of lignin peroxidase in the manner expected of a true substrate for the enzyme. For this reason, the order of additions to the reaction mixture is important and should be: first, ligninase; then, veratryl alcohol (when used), and $H_2O_2$; and finally, coal substrate, typically two to five minutes after addition of the $H_2O_2$. The system should be saturated with $O_2$ at the time the coal substrate is introduced. When coal substrate is added before $H_2O_2$ or veratryl alcohol, activity is lower.

Bovine serum albumin (BSA) appears to have a high affinity for coal, since the presence of BSA in the reaction assay (e.g., at 30 $\mu g/ml$) prevents the inhibition cf ligninase-catalyzed oxidation of veratryl alcohol by coal substrate (up to 18 $\mu g$ of Fraction IIIb/ml). However, adding BSA (30 $\mu g/ml$) after the enzyme had come in contact with the coal did not restore the activity.

Ligninase acts on aqueous coal substrate (e.g., Fraction IIIb described below) to catalyze the depolymerization of coal polymer to lower molecular weight compounds. In a 0.5–1.0 ml assay system buffered with 20 mM sodium tartrate, pH 3.0, (or 10 mM 2,2-dimethylsuccinate (DMS), pH 4.5) containing 0.04–0.2 U/ml ligninase, 0.1 mM $MnSO_4$, 0.1% Tween-20, 0.45–1.0 mM $H_2O_2$ and coal Fraction IIIb (100 $\mu l/1.0$ ml total volume of reaction mixture equivalent to 0.3 mg of carbon), purged with 100% $O_2$ and incubated at 37° C., a shift in the molecular weight distribution toward a lower molecular weight form was observed by conventional gel permeation high performance liquid chromatography, as described below, after between 4 and 24 hours of incubation. The coal peak, detectable before enzyme treatment, decreased greatly in size after enzyme treatment and a new peak of lower molecular weight compounds was generated, after such treatment, as evidenced by chromatographs.

In experiments where soluble coal polymer was in excess, gel permeation high performance liquid chromatography (HPLC) revealed that ligninase failed to elute at its characteristic elution volume after enzymatically treating coal substrate. Rather, it is eluted with the coal substrate and depolymerization products thereof, thereby often masking a disappearance of coal polymer upon enzyme treatment. In a modification of the method, an acetone-dimethylformamide (DMF) treatment was employed after enzymatic depolymerization to dissociate coal substrate, and fragments derived therefrom, from ligninase. If, after incubation for 24 hours with ligninase, the reaction mixture was treated with acetone-dimethylformamide (1:1), evaporated to dryness, and the residue dissolved in an appropriate buffer for chromatography, many new peaks, of molecular weight lower than that of the coal substrate, were present which were absent from the control lacking ligninase. These results indicate that ligninase can substantially depolymerize polymeric substituents present in coal.

Methods for recovering ligninase from the white-rot basidiomycete Phanerochaete chrysosporium are known, as are methods for culturing the fungus. A typical fungal culturing method is disclosed in Example Six.

A preferred method for recovering the enzyme from the culture media of the fungi is disclosed in Example Seven, and is also part of the present invention. With respect to this preferred method of the invention for isolating lignin peroxidase from unconcentrated lignin peroxidase-containing, mycelia-free fungal culture media (e.g. P. chrysosporium culture medium), affinity chromatography of the mycelia-free medium over a Macrosorb KAX.DEAE (Sterling Organics US, New York, N.Y., USA) column and specific elution of the enzyme therefrom is involved. Most preferred is Macrosorb KX6.DEAE, the Macrosorb KAX.DEAE which has 6% (w/w) cross-linked agarose in the Kieselguhr matrix. The surprisingly rapid and advantageously high-yield isolations attainable with the method are associated with the incompressibility of, and the high flow rates attainable with, a chromatographic matrix such as the Macrosorb KAX Kieselguhr-cross-linked agarose composites. Thus, although Macrosorb KX6.DEAE is most preferred, Macrosorb KAX.-DEAE supports with different percentages of cross-linked agarose (e.g., Macrosorb KX2.DEAE with 2% cross-linked agarose or Macrosorb KX4.DEAE with 4% cross-linked agarose) or any DEAE-derivatized chromatographic matrix material which is essentially incompressible and has a high flow rate for water could be employed. Thus, using as a standard the product "Macrosorb KA", which can be obtained from Sterling Organics US, New York, New York USA and is an essentially incompressible, high flow rate matrix material which is a composite of macroporous Kieselguhr in which the macropores are completely filled with agarose, a DEAE-derivatized chromatographic matrix material which, at 20° C and 1 atmosphere pressure is at least as incompressible as, and under a pressure gradient of 1 atmosphere per meter has a flow rate for water at least as great as Macrosorb KA composite, would also be suitable in the enzyme isolation method of the invention.

Reference herein to "mycelia-free," "unconcentrated" culture medium means medium as it comes from a culture and that is untreated except to render it substantially free of mycelia, by any method known in the art, such as centrifugation or passing through glass wool or a large pore filter material or the like through which the solution phase of the medium passes readily under the force of gravity and except to dilute the mycelia-free medium from 0-fold (no dilution) to up to about 10-fold with an aqueous solution that will not adversely affect the lignin peroxidase(s) in the medium. Preferred for dilution is a low ionic strength buffer (ionic strength less than about 0.2 molal) with a pH between about 6 and 8.

Thus, the method of the invention for obtaining lignin peroxidase from the medium of a culture in which the enzyme is made entails, as the essential steps, rendering said medium mycelia-free, optionally diluting the mycelia-free medium by a factor of up to about 10 with an aqueous buffer, passing the mycelia-free and optionally diluted medium over a DEAE-derivatized chromatographic matrix material which, at 20° C. and 1 atmosphere pressure is at least as incompressible as, and under a pressure gradient of 1 atmosphere per meter has a flow rate for water at least as great as Macrosorb KA, and then eluting the lignin peroxidase from the DEAE-derivatized material. Methods of eluting lignin peroxidases from DEAE-derivatized chromatographic supports are known in the art. Optionally, the eluate then can be pressure concentrated up to about 10-fold, such as by employing a pressure cell from, for example, Amicon Corp. (Danvers, Massachusetts, USA), with a suitable membrane (e.g., a YM-10 membrane), or, with or without such concentration step, can be treated further to obtain an highly pure lignin peroxidase preparation.

During enzyme recovery and in connection with treating coal substrate with ligninase, enzyme activity is determined spectrophotometrically at 310 nm, from the rate of oxidation of veratryl alcohol to veratraldehyde. One unit (U) of ligninase (lignin peroxidase) activity is defined as the amount of enzyme catalyzing the oxidation of 1 $\mu$mole of veratryl alcohol per minute in the assay protocol reported by Tien and Kirk, supra.

The use of ligninase to degrade suitable substrates which are solubilized from lignite and subbituminous coal, according to the method of the invention, is illustrated in Example Eight. For P. chrysosporium lignin peroxidase, the reaction is carried out at ambient pressure (approximately 1 atm.) and 37° C. in the presence of $O_2$ for up to 24 hours in a reaction mixture containing the following: 20 mM sodium tartrate adjusted to pH 3.0, containing 0.1 mM $MnSO_4$, 0.1% Tween-20, 0.45–1.0 mM $H_2O_2$, 0.04–2.0 U/ml lignin peroxidase and aqueous-soluble coal substrate. The coal substrate is preferably added and the depolymerization thereby initiated several minutes after $H_2O_2$ is introduced into the reaction mixture. At the time the coal substrate is added, the mixture is preferably saturated with $O_2$. Substances, such as serum albumin, may be present to reduce inhibition of ligninase by the substrate. It has been found that the presence of veratryl alcohol in the reaction mixture increases the observed rate of coal depolymerization by the ligninase (i.e., possibly by serving a mediator role in oxidation reactions, by enzyme-catalyzed formation of a veratryl alcohol cation radical which functions as an oxidant with regeneration of veratryl alcohol. See Haemmerli et al., J. Biol. Chem. 261, 6900–6903 (1986)).

The following examples are included to aid in understanding the invention. Such examples are for illustrative purposes only and are not meant to limit the scope of the appended claims. All examples are carried out at ambient (approx. 1 atm.) pressure.

EXAMPLE ONE

Methods for Treating Coal Samples With Nitric Acid

Prior to being fractionated to isolate an aqueous-soluble subfraction for enzymatic depolymerization according to the invention, the coal samples are partially oxidized with limited amounts of nitric acid at a temperature between about 15° C. and about 70° C. Methods for nitric acid treatment of carbonaceous compounds, including coal, are known. See for example, Schultz et al., U.S. Pat. Nos. 4,052,448; 4,137,418 and 4,235,728. Thus, a sample of coal is pulverized such that at least 50 wt.% passes through a 40 mesh (U.S. scale) screen. The pulverized coal is then suspended for about 0.5 hour to about 10 hours (typically 2 to 6 hours), at between about 10 wt % to about 20 wt %, in an aqueous solution of between about 10% and about 70% (typically about 20% to about 40%) nitric acid at a temperature below 70° C. (typically between about 15° C. and 50 ° C). After the reaction, the solids are separated from the solution by any mechanical means, typically centrifugation, and dried in air or under vacuum without heating above 70° C. These or other known methods can be used to oxidize the coal samples prior to preparation of an aqueous-soluble fraction for enzymatic depolymerization.

EXAMPLE TWO

A Method for Fractionating Coal to Produce an Aqueous-Soluble Polymeric Subfraction Extract Suitable for Enzyme-Catalyzed Depolymerization Prior to being enzymatically depolymerized, the nitric acid-oxidized coal samples are fractionated to produce a polymeric subfraction extract that is soluble in aqueous solution at pH 2.5–5, and that is suitable as a substrate for the degrading enzyme. This example illustrates a method for producing one such suitable polymeric subfraction substrate.

One gram of dried, powdered North Dakota lignite, previously treated as a slurry with nitric acid as described in Example One, was suspended in 100 ml of 1N NaOH and the suspension stirred for 30 minutes. The suspension was then centrifuged at 4° C. for 15 minutes at 10,000 x g to pellet a black precipitate, which was discarded. A clear, very dark supernatant solution, referred to as Fraction I, was saved.

Fraction I was adjusted to pH 3.5 with 6 N HCl and then centrifuged as above. This second centrifugation yielded a brown pellet and a clear yellow supernatant, which was removed and discarded. The clear yellow supernatant is referred to as Fraction II.

The brown pellet from the second centrifugation was resuspended in 50 ml of water, the resulting suspension was allowed to sit for 20 minutes, then centrifuged as above. This third centrifugation step yielded a brown pellet and a brown supernatant. The brown supernatant, the solute of which is referred to as Fraction IIIa, was saved. The brown pellet from the third centrifugation step was resuspended in 50 ml of water, the resulting suspension was allowed to sit for 20 minutes and then centrifuged as above. The resulting supernatant, the solute of which is referred to as Fraction IIIb, was saved.

The solution of Fraction IIIb may be used without dialysis or, as in this Example, it may be dialyzed against 50 mM EDTA in 20 mM sodium tartrate, pH 3.7, and then against either 20 mM sodium tartrate, pH 3.7, or against deionized water. BRL Prepared Dialysis Tubing (Bethesda Research Laboratories, Gaithersburg, MD, molecular weight exclusion 12,000–14,000 daltons) was used in the dialyses. The resultant, dialyzed solution of Fraction IIIb contains a coal subfraction that is suitable as a substrate for enzymatic depolymerization according to the present invention. If the solution of Fraction III(b) is to be used without dialysis, it is preferable to titrate it to attain a pH around pH 3. Further, it may be advantageous from the standpoint of yield to combine Fractions IIIa and IIIb, if the former contains at least about 20% of the carbon content of the latter. (The carbon content of Fraction IIIa, relative to that of IIIb, has been found to vary considerably from preparation to preparation.)

The carbon content of the various Fractions can be determined by the dichromate-sulfuric acid method of Johnson, J. Biol. Chem., 181:707 (1949). The carbon content of the Fractions, expressed in relative terms, determined by this method for a representative preparation is given in Table I.

TABLE I

| Carbon Content of Various Coal Fractions | |
|---|---|
| Coal Fraction | Carbon Content (%, Relative to 1% Powdered Coal Suspension) |
| 1% powdered coal suspension | 100 |
| Alkaline Extract (Fraction I) | 50 |
| Fractions IIIa and IIIb (together) | 35 |

EXAMPLE THREE

Characterization of a Subfraction Suitable for Depolymerization in Accordance With the Invention The Fraction IIIb from the lignite coal sample, fractionated as described in Example II, was characterized as follows:

1. Solubility

Coal polymer Fraction IIIb was soluble in water, dimethyl formamide, dimethyl sulfoxide, and tetrahydrofuran; sparingly soluble in methanol; and insoluble in acetone, ethyl acetate, acetonitrile, isopropanol, hexane, and toluene.

2. Absorbance Spectrum

The absorbance spectrum of a 1:200 dilution of the solution of Fraction IIIb is characterized by an approximately linear increase in absorbance as a function of decreasing wavelength beginning at about 400 nm and continuing to about 200 nm. The absorbance at 254 nm was used to monitor elution of coal polymers from gel filtration chromatographic columns.

3. Molecular Weight Distribution

The molecular weight distribution of Fraction IIIb components was determined by conventional gel permeation chromatography.

In anticipation of the task of detecting and recovering from the reaction mixture the composition resulting from enzymatic depolymerization of the coal substrate, gel permeation matrix materials were evaluated. It was first determined that coal polymers of Fraction IIIb would adsorb strongly at pH 3.5 to the porous, nonpolar vinyl polymer support sold as Fractogel TSK ™ (EM Industries, Inc., Gibbstown, N.J., U.S.A.), but would have low or no affinity for the support at pH 12 or in dimethylformamide. On the other hand, it was found that the material chromatographed normally in 0.02M potassium phosphate, 0.5 % Tween 80, pH 7, on dextran-based gel permeation media or silica-based HPLC supports. Therefore, the highly polar dextran supports are preferable and are used in analysis of soluble coal polymer (Fraction IIIb) and enzymatic depolymerization products therefrom.

Molecular weight distribution of Fraction IIIb components was determined by concentrated conventional gel permeation chromatography on Sephadex G-75 and G-200 using Blue Dextran [MW greater than $2 \times 10^6$ daltons] and $K_3Fe(CN)_6$, [MW=422 daltons] as standards. The column was developed with 0.02M potassium phosphate, 0.5% Tween 80, pH 7. The fraction consisted predominantly of two molecular weight classes of components. One class, which was observed visually as a brown band and by absorbance at 254 nm as a relatively symmetrical sharp peak, migrated with Blue Dextran on Sephadex G-75 and moved slightly slower than Blue Dextran on Sephadex G-200. The second class of components, which was observed visually as a faint brown band but could not be seen by absorbtion at 254 nm, moved slightly slower than potassium ferricyanide on both G-75 and G-200.

4. Summary

The analyses outlined in this example, taken in conjunction with carbon content data shown in Table I, demonstrate that Fraction IIIb includes a significant fraction of carbon from coal, and has a population of organic polymers with a molecular weight greater than about 75,000 daltons and less than about 2,000,000 daltons that are soluble in an aqueous solution at pH 3.5, ionic strength less than about 0.1 molal and room temperature.

EXAMPLE FOUR

An Alternate Method for Fractionating Coal to Produce a Polymeric Subfraction Suitable for Depolymerization This example illustrates a second method for fractionating and extracting a coal sample to provide a water-soluble polymeric subfraction suitable as a substrate for enzymatic depolymerization by ligninase in the presence of oxygen and hydrogen peroxide.

A sample of German subbituminous coal was ground to a powder and treated with 20% nitric acid for 1 hour at 50°–70° C. so as to introduce into the acetone-insoluble, alkali-soluble fraction one mole of carboxyl groups in about 325 g of material. The dried, oxidized coal was then fractionated essentially according to the method disclosed in Example Two, except for the following modifications designed to lower the amount of alkali the coal sample was subjected to.

Specifically, 1 gram of the dried, oxidized pulverized subbituminous coal was suspended in 100 ml of water. 6 N NaOH was added until the pH of the suspension was about pH 10–11 and the mixture stirred at room temperature for 30 minutes. Centrifugation, as in Example Two, yielded a supernatant (Alkaline Extract Supernatant) to which 6N HCl was added to bring the pH to 3.5. The pH 3.5 suspension was stirred for 30 minutes and centrifuged as before and the supernatant saved. Sodium chloride was added to the supernatant to 1 M concentration and after 30 minutes the supernatant with added NaCl was centrifuged as before. The resulting yellow supernatant was discarded. The pellet was suspended in 100 ml of $H_2O$, then left at room temperature for about 12 hours. The mixture was centrifuged as before and the dark brown supernatant (pH 3.5) taken as the solution of the final, water-soluble coal polymer subfraction (Fraction IIIb). Before use in enzymatic depolymerization, this solution was dialyzed against distilled water using the 12,000–14,000 dalton cut-off BRL prepared dialysis membrane. All other parts of the procedure were as described in Example Two.

The relative carbon content of the Fractions obtained by the alternative fractionation method of Example Four is shown in Table II.

TABLE II

Carbon Content of Various Fractions of German Subbituminous Coal
(The analytical procedure followed was identical to that given in Table I.)

| Coal Fraction | Relative Carbon Content |
| --- | --- |
| 1% powdered suspension of oxidized coal | 100 |
| Alkaline Extract Supernatant | 34 |
| Final Coal Polymer Subfraction, pH 3.5, prior to dialysis | 28.3 |

EXAMPLE FIVE

Characterization of the Water Soluble Coal Polymer Subfraction Produced by the Method of Example Four Characterization of the water soluble coal polymer subfractions produced according to the alternative method of Example Four showed, on gel permeation HPLC chromatography, a somewhat heterodisperse major peak with a molecular weight of less than 2 million daltons but greater than 80,000 daltons and also some other minor peaks of high molecular weight material, but of lower molecular weight than the primary peak. There were no intermediate or low molecular weight peaks. Gel permeation HPLC chromatography was performed with a Synchropak GPC 300 column (Synchrom Inc., Lafayette, Indiana, U.S.A.,), a bonded carbohydrate coated silica-based support equilibrated with 0.02 M potassium phosphate buffer, pH 7, 0.5 % Tween 80, at a flow rate of 0.24 ml/min.

EXAMPLE SIX Culture of *Phanerochaete chrysosporium*

This example illustrates culture of *Phanerochaete chrysosporium*, a white-rot basidiomycete known to produce ligninase, and follows published procedures.

Cultures of *Phanerochaete chrysosporium* can be obtained from rotting wood, or from public culture collections such as the American Type Culture Collection, Rockville, Maryland ("ATCC") or the culture depository of the U.S. Department of Agriculture Northern Regional Research Laboratory, Peoria, Illinois ("NRRL"). Phanerochaete chrysosporium Burds strain ME-446 carries ATCC Deposit No. 34541; Burds strain BKM-F-1767 is identified by ATCC Deposit No. 24725. P. chrysosporium strain SC26 carries NRRL Accession No. 15978; see Farrell et al., supra.

Cultures of Phanerochaete chrysosporium Burds strain ME-446 (ATCC No. 34541) were grown in Erlenmeyer flasks in the nitrogen-limited basal medium BIII described by Kirk T. K., et al., Enzyme Microb. Technol. 8:27–32 (1986) with the following modifications and addition: 10 mM 2,2-dimethylsuccinate (DMS), pH 4.5, 0.5% glucose, 10 μg/ml thiamine, 0.1% (w/v) Tween-20, and 0.4 mM veratryl alcohol. Phanerochaete chrysosporium also exhibited good growth with 0.5% glycerol or 1.0% glucose as the carbon source, in place of 0.5% glucose. All cultures were grown at 39° C. on a rotary shaker (200 rpm). The culture sizes were as follows: 10 ml per 125 ml Erlenmeyer flask; 300 ml per 1 liter Erlenmeyer flask; 500 ml per 2 liter Erlenmeyer flask. All cultures were purged daily with 100% $O_2$.

Cells from the most active cultures (i.e., those producing the greatest amounts of ligninase activity) were collected and used as an inoculum for new cultures. Inoculum cells are prepared from cultures grown in a stationary 1 liter Erlenmeyer flask containing 50 ml of the modified, nitrogen-limited BIII medium described above. Cell cultures were harvested 3-7 days after seeding and homogenized in a sterile Potter-Elvehjem homogenizer until a very fine homogeneous suspension was obtained. The suspension, after being diluted 1:10 in fresh medium, was used to seed other Erlenmeyer flask cultures.

It was found that ligninase production was influenced by the homogeneity of the inoculum used to seed the culture. Seeding with very fine suspensions of cells gave rise to the preferred, numerous tiny mycelial pellets; seeding with heterogeneous suspensions containing large aggregates of cells gave rise to mycelial mats (See Faison, B. D. and Kirk, T. K. Appl. Environ. Microbiol 49:299-304 (1985)). Measurements of the amount of ligninase present in the extracellular culture fluid showed that the level of ligninase activity was highest in cultures containing numerous tiny pellets and lowest in cultures in which most of the cells had aggregated into mats. Ligninase activity was never detected in extracts of mycelial pellets or mats.

As a convenient indicator of the appearance of ligninase activity in the extracellular culture fluid, an abrupt change in the color of the fungal pellets (from white to blackish brown) coincides with an increase in enzyme concentration. The level of ligninase activity peaked within 48 hours after culture growth stopped, following which there was a dramatic 30%-50% decrease in enzymatic activity over the next 24 hour period.

EXAMPLE SEVEN

Preparation of Ligninase

This example illustrates preparation of ligninase from cultures of Phanerochaete chrysosporium using a diethylaminoethyl (DEAE)-derivatized Kieselguhragarose matrix support, wherein the agarose is DEAE-derivatized.

Methods for purifying ligninase from cultures of Phanerochaete chrysosporium are known. See for example Jager, A., Appl. Environ., Microbiol., 50:1274-1278 (1985). Tien and Kirk, supra, and Renganathan, V. et al. Arch. Biochem. Biophys. 241:301-314 (1985). Methods for determining the specific activity of preparations of the enzyme are also known. See, for example, Tien and Kirk, supra. The enzyme yield from these known methods is quite low.

To increase the yield and to prepare for scaling up the culture volume, a novel recovery method was developed, which is based on the ion-exchange properties of the diethylaminoethyl (DEAE) group on a virtually incompressible solid support which allows high liquid flow rates. Such supports include the Kieselguhr-based, DEAE-derivatized, cross-linked agarose supports known as Macrosorb KAX.DEAE, sold by Sterling Organics US, New York, N.Y., U.S.A. Macrosorb KAX.DEAE supports are composed of highly porous spheres of fused Kieselguhr (a form of diatomite that is more than 90% silica) containing, in the interior of the spheres, cross-linked, DEAE-derivatized agarose. The supports are provided with different percentages of cross-linked agarose in the Kieselguhr matrix. Thus, Macrosorb KX2.DEAE has 2% cross-linked agarose, Macrosorb KX4.DEAE has 4% cross-linked agarose, and Macrosorb KX6.DEAE has 6% cross-linked agarose.

Chromatography of mycelia-free, unconcentrated culture medium of P. chrysosporium cultures with Macrosorb KAX.DEAE supports provides, surprisingly, much higher yields of the enzyme than have been achieved by prior art methods. Further, isolation of lignin peroxidase from such culture media proceeded much more rapidly with such chromatography using Macrosorb KAX.DEAE supports than with prior art methods, involving ultrafiltration and dialysis of culture medium prior to chromatography.

First, seven to twelve day old Phanerochaete chrysosporium cultures were filtered through glass wool to remove mycelia and spores. 500 ml of mycelium-free broth was diluted with 500 ml of 10 mM potassium phosphate buffer, pH 7.0 and pumped through a 1.0 x 50 cm column of the Macrosorb KX6.DEAE equilibrated with 10 mM potassium phosphate buffer, pH 7, at the rate of 5.0 ml/min. The column was washed with two bed volumes of the equilibration buffer. A gradient of 500 ml of 0 to 0.2 M NaCl-10 mM potassium phosphate buffer, pH 7, was then run. Only a few minor peaks of ligninase activity were observed. One bed volume of either 10 mM sodium tartrate buffer, pH 3.0, or of the 0.2 M NaCl-10 mM potassium phosphate buffer, pH 7, was then run over the column and the major portion of the activity eluted in 55 ml. The peroxidase was then rapidly (1 hour) concentrated 10-fold in an Amicon pressure cell (Amicon Corp., Danvers, Massachusetts, USA) with a YM-10 membrane. Recovery was about 90% (88%-93%), and advantageously in addition, the slime, that accumulates during the ultrafiltration of culture media used in prior art methods, was not observed. Results of a typical purification are tabulated in Table III. All of the above procedures, starting with filtration of culture medium, were carried out at 4° C. The concentrated enzyme solution from the Macrosorb KX6.DEAE column was dialyzed against deionized distilled water and the enzyme stored as lyophilyzed powder at −20° C. Further, manganese peroxidase, which has been reported to be present in some lignin peroxidase-containing solutions, was virtually absent from the lignin peroxidase preparation ($<1\%$ of lignin peroxidase activity), as determined using the assay for manganese peroxidase described by Glenn, J. K. & H. Gold, Arch. Biochem. Biophys. 242, 329-341 (1985).

TABLE III

| Recovery of Ligninase from Culture Medium | | | | |
|---|---|---|---|---|
| Fraction | Volume (ml) | U/ml | Units | Recovery |
| Culture broth | 500 | 0.15 | 75 | 100% |
| Macrosorb KAX.DEAE eluate | 55 | 1.20 | 66 | 88% |

EXAMPLE EIGHT

Enzymatic Depolymerization of a Soluble Polymeric Coal Substrate

Enzymatic depolymerization of the final soluble subbituminous coal polymer substrate described in Example Four was carried out using reaction mixtures containing ligninase (1 Unit, Macrosorb preparation, as described in Example Seven) in 20 mM sodium tartrate buffer, pH 3.0, 0.1 mM MnSO$_4$, 0.1% Tween-20, 0.1 ml of the dialyzed Fraction IIIb solution described in Example IV (equivalent to 0.3 mg of carbon), and 0 or 2 mM veratryl alcohol, in a volume of 1.0 ml. H$_2$O$_2$ was added to 0.45 mM together with the veratryl alcohol, if used, and the reaction mixture held for 5 minutes before the addition of the coal polymer solution. Tubes were incubated at 37° C. with shaking and were oxygenated by purging 100% $O_2$ through the solution every fifteen minutes. Controls without coal polymer, but with and without veratryl alcohol, were also run.

Samples of the reaction mixture were analyzed by gel permeation HPLC on a Synchropak GPC column as described above. HPLC analyses of the samples of the reaction mixture revealed that the major, soluble polymer coal peak became smaller with time. The analyses also revealed that veratryl alcohol increased the rate of ligninase-catalyzed coal depolymerization.

In some experiments many new small peaks indicative of low molecular weight compounds were observed in the HPLC analyses of the enzyme-containing reaction mixtures, which small peaks were lacking in the HPLC analyses of the enzyme-free control mixtures. In other experiments, no peaks corresponding to lower molecular weight fragments were detected even as the size of the major coal polymer peak decreased with time. The absence of the smaller fragments in some samples, while the major coal polymer peak decreased, is believed to be due to (1) the enzymatically catalyzed cleavage of aromatic rings by ligninase and accompanying loss of UV absorbance as reported by Umezawa, T. and Higuichi, T., Agri. Biol. Chem. (Japan) 51:2281–2285 (1987); and (2) the formation of so many different molecular weight fragments which separate on gel permeation HPLC that the concentration of each fragment is too low to be detected.

Similar experiments were run with soluble Fraction IIIb (or Fraction IIIb together with Fraction IIIa), prepared with North Dakota lignite coal samples as described in Example Two. Similar results were obtained, indicating the enzyme depolymerized the soluble coal polymer.

In both experiments a small amount of material was formed with a molecular weight greater than that of the starting material. This is consistent with non-enzymatic condensation of fragments to yield higher molecular weight polymers, as would be expected of a cation radical-based reaction mechanism, as has been established for lignin peroxidase.

EXAMPLE NINE

Alternate Enzyme-Catalyzed Depolymerization Reaction

Enzyme-catalyzed depolymerization of coal polymer in Fraction IIIb (See Example Two) was carried as follows: A reaction mixture with a volume of 0.5–1.0 ml containing 0.2–1.0 U/ml ligninase, 0.1 mM $MnSO_4$, 0.1% Tween-20, 0.45–1.0 mM $H_2O_2$, and buffered at pH 3.0 with 20 mM sodium tartrate was prepared. Fraction IIIb was added to give a final ratio of 0.1 ml Fraction IIIb solution/1.0 ml total reaction sample. The reaction sample was purged with 100% $O_2$ and incubated at 37° C. for 24 hr.

0.1 ml of reaction sample and 0.2 ml acetone/dimethylformamide (1:1) were mixed by shaking and centrifuged for 2 minutes in an Eppendorf centrifuge to remove denatured protein. The supernatant was removed and air dried to remove acetone. The residue was dissolved in 10 mM phosphate buffer, pH 7, 0.5 % Tween 80 and subjected to gel permeation HPLC analysis, which revealed a series of discrete, smaller, low molecular weight peaks.

While the invention has been described in the present specification with some specificity, those of ordinary skill in the pertinent art will recognize variations and modifications of what has been described that are within the spirit of the invention. Such modifications and variations are intended to be within the scope of the invention as described and claimed herein.

Various features of the invention are defined in the following claims.

What is claimed is:

1. A method for enzymatically depolymerizing polymeric substituents of coal comprising combining in an aqueous solution, in which a lignin peroxidase is enzymatically active, an aqueous soluble polymeric coal substrate, the lignin peroxidase, hydrogen peroxide and oxygen.

2. A method according to claim 1 wherein the lignin peroxidase is from Phanerochaete chrysosporium.

3. A method according to claim 2 wherein the oxygen is provided to the reaction mixture by purging.

4. A method according to claim 3 wherein the aqueous solution comprises veratryl alcohol.

* * * * *

UNITED STATES PATENT AND TRADEMARK OFFICE
CERTIFICATE OF CORRECTION

PATENT NO. : 4,960,699

DATED : October 2, 1990

INVENTOR(S) : Wood, et al.

It is certified that error appears in the above-identified patent and that said Letters Patent is hereby corrected as shown below:

On the title page: Under "References Cited, U.S. PATENT DOCUMENTS" insert --4,882,274 11/89 Pyne, Jr. et al.--.

Column 1, Line 67: Change "lining" to --lignin--.

Column 2, Line 46: Change "Farre)l" to --Farrell--.

Column 3, Line 62: Change "(o)" to --(c)--.

Column 12, Line 45: Change "TSK TM" to TSK$^{TM}$--.

Column 15, Line 35: Change "Kieselguhragarose" to --Kieselguhr-agarose--.

Signed and Sealed this

Third Day of March, 1992

Attest:

HARRY F. MANBECK, JR.

*Attesting Officer*   *Commissioner of Patents and Trademarks*